United States Patent [19]

Babler

[11] Patent Number: 5,231,232

[45] Date of Patent: Jul. 27, 1993

[54] METHOD OF PREPARING C-18 KETONES USED IN THE MANUFACTURE OF VITAMINS E AND K

[75] Inventor: James H. Babler, Chicago, Ill.

[73] Assignee: Loyola University of Chicago, Chicago, Ill.

[21] Appl. No.: 807,462

[22] Filed: Dec. 18, 1991

[51] Int. Cl.$^5$ ............................................. C07C 45/69
[52] U.S. Cl. .................................... 568/393; 568/391
[58] Field of Search ...................... 568/393, 417, 391; 585/534

[56] References Cited

U.S. PATENT DOCUMENTS

| | | | |
|---|---|---|---|
| 4,002,684 | 1/1977 | Fraunberg | 568/393 |
| 4,625,066 | 11/1986 | Elbe | 568/417 |

FOREIGN PATENT DOCUMENTS

| | | | |
|---|---|---|---|
| 0045861 | 2/1982 | European Pat. Off. | 568/393 |
| 56-65840 | 6/1981 | Japan | 568/393 |

OTHER PUBLICATIONS

F. Gottwalt Fischer, Kurt Löwenberg; *Die Synthese des Phytols;* Annalen der Chemie, 475, 1929; pp. 183–204.

Robert S. Harris, Ira G. Wool; *Chemistry of Vitamin E;* Vitamins and Hormones: Advances in Research and Applications; Vol. 20, 1962; pp. 389–405.

J. W. K. Burrell, R. F. Garwood, L. M. Jackman, E. Oskay, B. C. L. Weedon; *Carotenoids and Related Compounds. Part XIV. Stereochemistry and Synthesis of Geraniol, Nerol, Farnesol and Phytol;* J. Chem. Soc., 1966; pp. 2144–2154.

Kikumasa Sato, Shioji Mizuno, Masao Hirayama; *A Total Synthesis of Phytol;* J. Organic Chemistry, vol. 32, Jan. 1967; pp. 177–180.

*Terpenes;* Chem. Abstracts, 100,279z, vol. 67, 1967; p. 9441.

*Aliphatic Compounds;* Chem. Abstracts, 109, 784h, vol. 75, 1971; p. 393.

E. W. Collington, A. I. Meyers; *A Facile and Specific Conversion of Allylic Alcohols to Allylic Chlorides without Rearrangement;* J. Organic Chemistry, vol. 36, No. 20, 1971; pp. 3044–3045.

C. Cahiez, A. Alexakis, J. F. Normant; *A Highly Stereoselective Preparation of 1,4- and 1,5-Alkadienes;* Synthesis, 1978; pp. 528–530.

Francis Barbot, Danielle Mesnard, Léone Miginiac; *Synthesis of γ-Unsaturated Methylketones;* Organic Preparations and Procedures, 10, 1978; pp. 261–266.

Ka-Kong Chan, Anthony C. Specian, Jr., Gabriel Saucy; *Synthesis of (2R,4'R,8'R) -α-Tocopheryl Acetate (i Vitamin E Acetate) Using [3,3] Sigmatropic Rearrangement;* J. Organic Chemistry, vol. 43, No. 18, 1978; pp. 3435–3440.

(List continued on next page.)

Primary Examiner—James H. Reamer
Attorney, Agent, or Firm—Marshall, O'Toole, Gerstein, Murray & Borun

[57] ABSTRACT

Methods of forming unsaturated C-18 ketones which can be used in the synthesis of Vitamins E and K$_1$ are disclosed. One procedure involves coupling a C-9 primary allylic halide to a carbonyl-group-containing C-9 terminal alkyne. A second, two-step procedure employs a C-4 bis allylic halide (molar excess) and a carbonyl-group-containing C-9 terminal alkyne to form a C-13 primary allylic halide. The C-13 primary allylic halide can then be converted to the desired C-18 ketone by reaction with 2-methyl-3-butyn-2-ol. Novel C-18 ketones (e.g., 14-hydroxy-6,14-dimethyl-10-methylene-5-pentadecen-7,12-diyn-2-one), C-13 allylic halides (e.g., 10-chloromethyl-6-methyl-5,10-undecadien-7-yn-2-one) and C-9 allylic halides (e.g., 6-chloromethyl-2-methyl-6-hepten-3-yn-2-ol) are formed in the process.

15 Claims, No Drawings

OTHER PUBLICATIONS

S. Terao, M. Shiraishi, K. Kato; *A Facile Synthesis of Allylic Alcohols;* Synthesis, 1979; pp. 467–468.

Noel Cohen, Rocco J. Lopresti, Gabriel Saucy; "*A Novel Total Synthesis of (2R,4'R,8'R) -α-Tocopherol (Vitamin E), Construction of Chiral Chromans from an Optically Active, Nonaromatic Precursor*", Journal of American Chemical Society, 101, 1979; pp. 6710–6716.

Tamotsu Fujisawa, Toshio Sato, Tatsuo Kawara, Kazuo Ohashi; *A Stereocontrolled Total Synthesis of Optically Active (R,R)-Phytol;* Tetrahedron Letters, vol. 22, No. 48, 1981; pp. 4823–4826.

Seiichi Takano, Masamichi Morimoto, Shigeki Satoh, Kunio Ogasawara; *Syntheses of Perillene and Rosefuran from Common Starting Materials;* Chemistry Letters, 1984; pp. 1261–1262.

Paul Mosset, René Grée; *Trimethylsulfonium Methylsulfate, A Simple and Efficient Epoxidizing Agent;* Synthetic Communications, 15, 1985; pp. 749–757.

Tuyêt Jeffery; *Copper (I) and Phase Transfer Catalysed Allylic Substitution by Terminal Alkynes;* Tetrahedron Letters, vol. 30, No. 17, 1989; pp. 2225–2228.

Michael Bulliard, Geneviève Balme, Jacques Gore, *Chloration Allylique D'Olefines De Type Isoprenique A L'aide Du Chlorure De Sulfuryle;* Tetrahedron Letters, vol. 30, No. 42, 1989; pp. 5767–5770.

METHOD OF PREPARING C-18 KETONES USED IN THE MANUFACTURE OF VITAMINS E AND K

BACKGROUND OF THE INVENTION

The present invention describes processes for the chemical synthesis of unsaturated C-18 ketones which can be readily converted to phytol (3,7,11,15-tetramethyl-2-hexadecen-1-ol) and isophytol (3,7,11,15-tetramethyl-1-hexadecen-3-ol). Both phytol and isophytol can be used in the manufacture of alpha-tocopherol (the most active vitamin E factor known to occur in nature), and in the synthesis of vitamin K. Novel chemical intermediates used in the preparation of isophytol and phytol are also disclosed herein, as well as procedures for synthesizing these intermediates.

Synthesis of phytol generally requires lengthy sequences of reactions as exemplified in the following references: B. C. L. Weedon, et al., *J. Chem. Soc. (C)*, 2144 (1966); K. Sato, et al., *J. Org. Chem.*, 32, 177 (1967); and T. Fujisawa, et al., *Tetrahedron Lett.*, 22, 4823–4826 (1981). F. G. Fischer and K. Löwenberg, *Ann.*, 475, 183–204 (1929), have reported a synthesis of phytol (and isophytol) utilizing the C-18 ketone (1) shown below as the key intermediate:

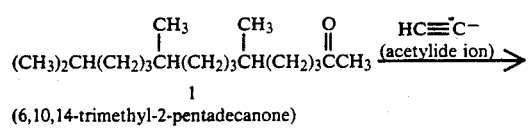
1
(6,10,14-trimethyl-2-pentadecanone)

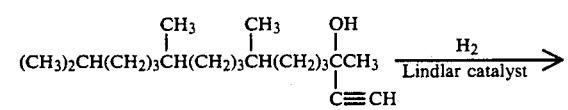

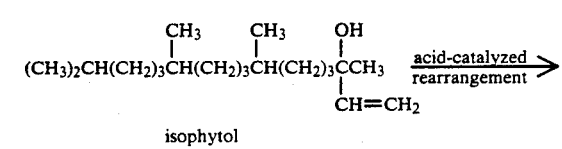
isophytol
(3,7,11,15-tetramethyl-1-hexadecen-3-ol)

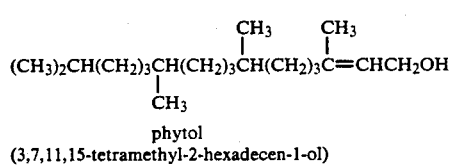
phytol
(3,7,11,15-tetramethyl-2-hexadecen-1-ol)

Treatment of either phytol or isophytol with the commercially available trimethylhydroquinone and an acid catalyst affords alpha-tocopherol, as outlined below [See: pages 392-3 in "Chemistry of Vitamin E" by O. Isler, et al.; a chapter in *Vitamins and Hormones: Advances in Research and Applications*, Volume 20, edited by R. S. Harris, et al. (Academic Press, 1962).

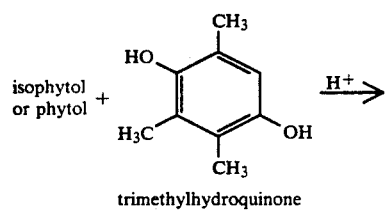
trimethylhydroquinone

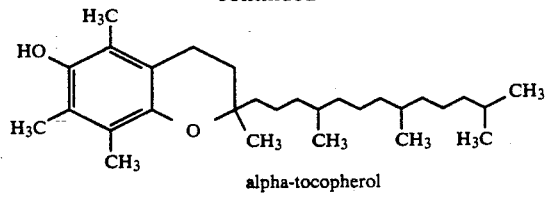
alpha-tocopherol

Other processes for synthesizing vitamins E and $K_1$ are illustrated in *Chem. Abstracts*, 67, 100,297z (1967); in a chapter in *Vitamins and Hormones: Advances in Research and Applications*, Volume 20, edited by R. S. Harris, et al. (Academic Press, 1962, pages 389–405); in N. Cohen, et al., *J. Am. Chem. Soc.*, 101, 6710 (1979); and, in K. Chan, et al., *J. Org. Chem.*, 43, 3435 (1978).

SUMMARY OF THE INVENTION

A. Formation of unsaturated C-18 Ketones

The method of the present invention produces the C-18 ketone (1) shown above, but obtained in a novel manner. In the processes disclosed herein, novel C-18 unsaturated ketones are prepared which possess the carbon skeleton of ketone 1, as well as the carbonyl group at position #2. Simple catalytic hydrogenation ($H_2$/Pd-C) of these unsaturated ketones affords the known C-18 saturated ketone (1).

These novel C-18 unsaturated ketones can be prepared by coupling C-9 primary allylic halides to a C-9 terminal alkyne that possesses a carbonyl group. Alternatively, the unsaturated C-18 ketone may be prepared by reacting a molar excess of a bis allylic halide of the formula $(XCH_2)_2C=CH_2$ with a C-9 terminal alkyne that possesses a carbonyl group, and coupling the resultant C-13 primary allylic halide with 2-methyl-3-butyn-2-ol.

The first procedure, wherein a C-9 primary (1°) allylic halide is coupled with a C-9 terminal alkyne having a carbonyl group (e.g., 6-methyl-5-octen-7-yn-2-one (2)), is shown below:

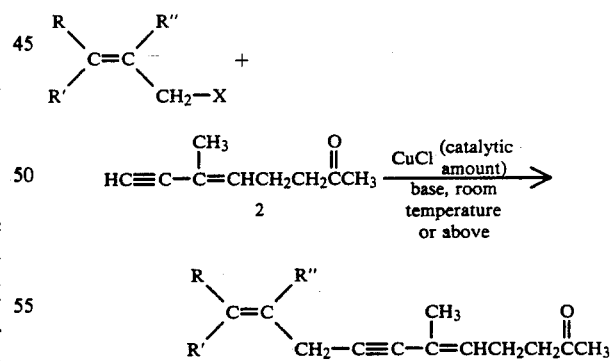

In the foregoing reaction, X is a halide group, preferably Cl or Br. R and R, are either both H, or one substituent is H and the other is a C-5 group selected from one of the following: $(CH_3)_2C(OH)C\equiv C-$, $CH_2=C(CH_3)C\equiv C-$, $(CH_3)_2CHCH_2CH_2-$, $CH_2=C(CH_3)CH_2CH_2-$, and $(CH_3)_2C=CHCH_2-$; R" is a C-6 group selected from one of the following: $(CH_3)_2C(OH)C\equiv CCH_2-$, $CH_2=C(CH_3)C\equiv CCH_2-$, $(CH_3)_2CHCH_2CH_2CH_2-$, $(CH_3)_2C=CHCH_2CH_2-$ and $CH_2=C(CH_3)CH_2CH_2CH_2-$, or R" is $CH_3-$.

This transformation proceeds at a reasonable rate at room temperature, although warming the mixture to accelerate the process may be desirable for certain systems. Yields of the coupled products are high (generally 70-95%), and few (if any) by-products were detected in the crude reaction product.

For its successful execution, the C-9 to C-9 coupling step requires:

(a) a C-9 primary allylic halide as defined above (one equivalent). Allylic chlorides are preferred for economic reasons. However, other 1° allylic halides may be used.

(b) one equivalent of a C-9 terminal alkyne selected from the group consisting of:

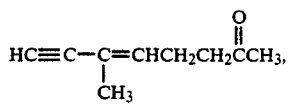

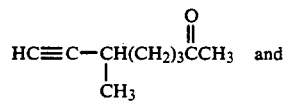

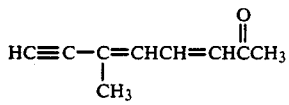

(c) a transition metal catalyst, preferably a copper (I) salt: Cuprous chloride is especially preferred, but copper (I) iodide (cuprous iodide) was also used with success.

(d) A base must be present for the coupling reaction to proceed. Due to the reactivity of 1° allylic halides with bases, the preferred base is one that is moderately weak (carbonate or bicarbonate) and non-nucleophilic (e.g., phosphate or carbonate bases). Preferred bases include sodium carbonate, potassium carbonate, $K_2HPO_4$ (potassium phosphate, dibasic or dipotassium hydrogen phosphate), and $Na_2HPO_4$. Tertiary (3°) amines could also be used as the base.

(e) Although use of a solvent is not necessary, solvents may accelerate the coupling reaction. The solvent can be protic or aprotic. Addition of polar solvents (e.g., acetonitrile, 1-methyl-2-pyrrolidinone, or N,N-dimethylformamide) accelerates the coupling reaction. The reaction proceeds more slowly if a less polar solvent (e.g., ethyl acetate) is added to the mixture.

(f) Addition of a catalytic amount (10% or less) of a phase-transfer catalyst is not necessary, but the presence of such a catalyst increases the reaction rate significantly. Various quaternary ammonium salts ($R_4N^+X^-$) will function as such a catalyst, including benzyltriethylammonium chloride and tetrabutylammonium chloride.

Novel C-18 unsaturated ketones which are formed in the course of C-9 to C-9 coupling reaction include:

a) 14-hydroxy-6,14-dimethyl-10-methylene-5-pentadecen-7,12-diyn-2-one b) 14-hydroxy-6,10,14-trimethyl-5,10-pentadecadien-7,12-diyn-2-one c) 6,14-dimethyl-10-methylene-5,14-pentadecadien-7,12-diyn-2-one d) 6-methyl-10-[4-methylpentyl]-5,10-undecadien-7-yn-2-one e) 6,10,14-trimethyl-5,10-pentadecadien-7-yn-2-one f) 6,14-dimethyl-10-methylene-5,13-pentadecadien-7-yn-2-one g) 6,10,14-trimethyl-5,10,13-pentadecatrien-7-yn-2-one As noted above, one of the desired unsaturated C-18 ketones can also be prepared by reacting a molar excess of a bis allylic halide of the formula $(XCH_2)_2C=CH_2$ with a C-9 terminal alkyne that possesses a carbonyl group, and coupling the resultant C-13 primary allylic halide with 2-methyl-3-butyn-2-ol. The bis allylic chloride (3), 3-chloro-2-chloromethyl-1-propene (commercially available from Aldrich or Fluka), is a preferred bis allylic halide. The C-9 terminal alkyne can be selected from the group consisting of:

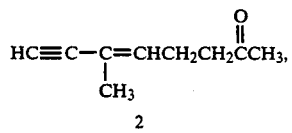

2

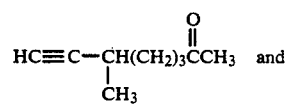

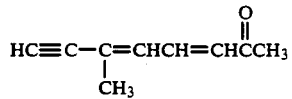

Enynone 2 is especially preferred.

The bis halide must be used in excess (10 equivalents or more) relative to the C-9 terminal alkyne to prevent undesired bis coupling (i.e., reaction at both allylic halide sites):

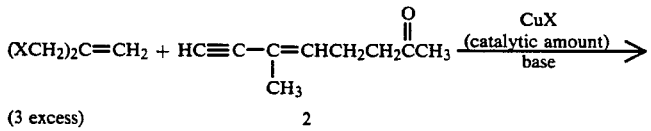

(3 excess)     2

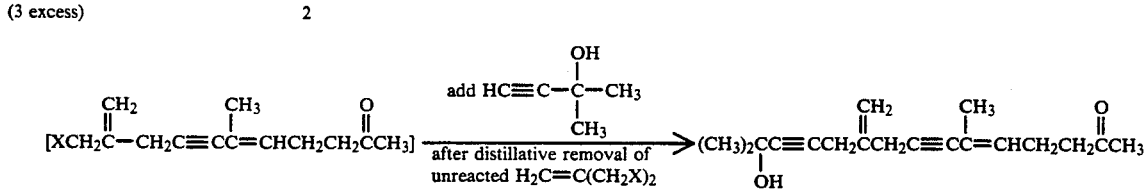

This same C-18 compound can also be prepared by coupling a C-9 allylic halide, as defined above, and enynone 2.

The product obtained by the reaction of bishalide 3 and enynone 2 is a novel C-13 allylic halide, viz, 10-halomethyl-6-methyl-5,10-undecadien-7-yn-2-one.

The coupling of terminal alkynes and primary allylic halides in the presence of a catalytic amount of a copper (I) salt is not a novel transformation per se. Several examples can be found in the chemical literature, as reported by T. Jeffery, *Tetrahedron Lett.*, 30, 2225 (1989). See especially the patents Jeffery cites in footnotes 4 and 5 in that paper.

However, the prior art does not disclose use of a reactant possessing a carbonyl group. Since enolizable ketones [i.e., those possessing acidic hydrogens bonded to the alpha carbon (next to the carbonyl)] can be alkylated by reactive primary allylic halides in the presence of a base, the following undesirable side-reaction might have been anticipated to occur:

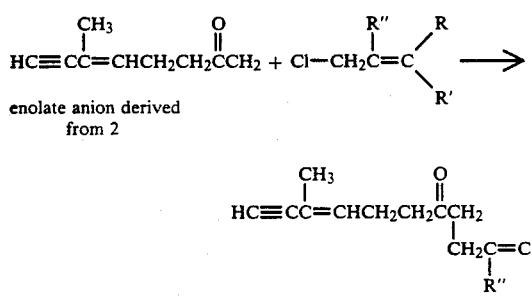

enolate anion derived from 2

Although one normally uses a stronger (e.g., alkoxide) base to generate enolate anions from ketones, some enolate formation is expected in the presence of potassium carbonate in polar organic solvents, especially those containing a hydroxyl group, since trace amounts of an alkoxide base might be generated in situ. Alkynes (under basic conditions) are also known to condense with ketones as shown below:

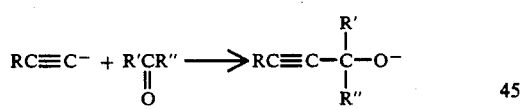

Due to the anticipated reactivity of the carbonyl group, priori, would have predicted the need for blocking the ketone (e.g., as an acetal derivative).

However, as illustrated by the synthesis shown in Example IV, hereafter, the combination of a hydroxyl-containing compound (2-methyl-3-butyn-2-ol), a ketone and a base [aqueous solutions of $K_2CO_3$ are strongly alkaline: pH approximately 12] does not result in the formation of the expected undesirable reaction products.

B. Synthesis of 6-Methyl-5-octen-7-yn-2-one.

The alkyne (e.g., enynone 2) used in the coupling step can be prepared in accordance with the procedure developed by L. Miginiac, et al., *Org. Prep. Proced. Int.*, 10, 261 (1978) outlined below:

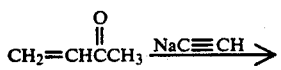

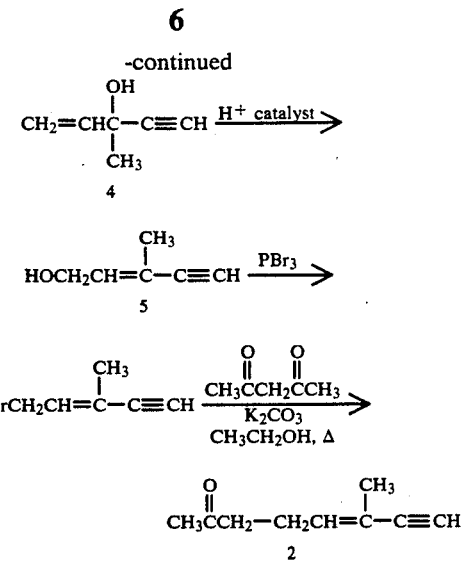

2, approximately 70% yield from alcohol 5 Alcohol 5 is commercially available from Aldrich or Fluka.

An alternate route to enynone 2 has been reported by P. I. Zakharova, et al., *Zh. Org. Khim.*, 7, 1137, (1971), and involved treatment of tertiary allylic alcohol 4 with 2-methoxypropene [see: *Chem. Abstracts*, 75, 109,784h (1971)]. Another route to the desired C-9 enynone is via the palladium-catalyzed alkylation of ester derivatives of acetoacetic acid

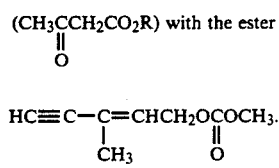

This latter ester can be obtained from alcohol 5 and methyl chloroformate

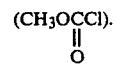

C. Routes to C-9 Allylic Halides Utilized in the Coupling Process.

Route I:

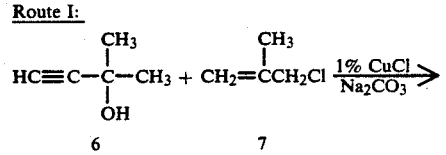

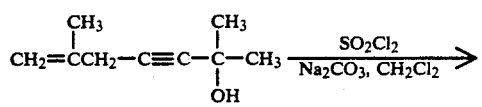

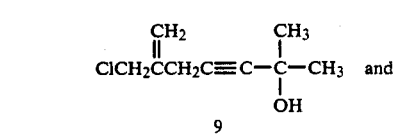

-continued

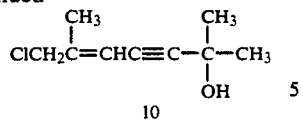
10

The starting reactants, 2-methyl-3-butyn-2-ol (6) and 3-chloro-2-methyl-1-propene (7) in this route are inexpensive and couple together to afford a novel alkene 8 (2,6-dimethyl-6-hepten-3-yn-2-ol) in high yield. Subsequent treatment of alkene 8 with sulfuryl chloride and sodium carbonate gives a mixture of allylic chlorides 9 and 10. This method of converting alkenes to allylic chlorides by use of SO$_2$Cl$_2$ and Na$_2$CO$_3$ was developed by J. Gore, et al., *Tetrahedron Lett.*, 30, 5767 (1989). More conveniently, 1° allylic chloride 9 can be obtained directly in high yield by coupling 2-methyl-3-butyn-2-ol (6) with a large excess of 3-chloro-2-chloromethyl-1-propene:

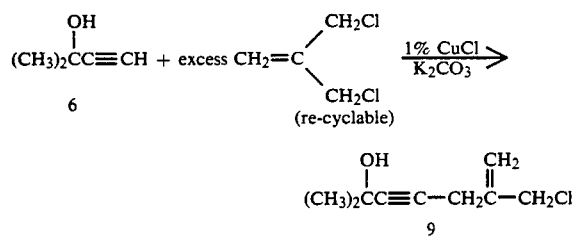

Route II:

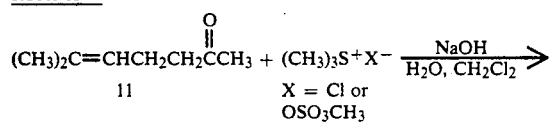

-continued (CH$_3$)$_2$C=CHCH$_2$CH$_2$CCH$_2$Cl and
              ‖
              CH$_2$
15

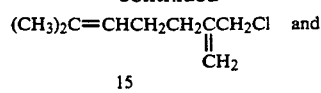
16

In the above route, commercially-available 6-methyl-5-hepten-2-one (11) was converted to epoxide 12 using a method developed by R. Gree, et al., *Synth. Commun.*, 15, 749 (1985). Isomerization of epoxide 12 to allylic alcohols 13 and 14 can be achieved by the method of S. Terao, et al., Synthesis, 467 (1979).

Allylic alcohol 13 can also be obtained in one step from 1-chloro-3-methyl-2-butene and 2-methyl-2-propen-1-ol, as described by S. Takano, et al., *Chem. Lett.*, 1261 (1984).

Novel C-9 allylic halides which can be formed by using one of the above processes and employed in the C-18 synthesis include:

a) 6-chloromethyl-2-methyl-6-hepten-3-yn-2-ol, the preferred C-9 allylic chloride
b) 7-chloro-2,6-dimethyl-5-hepten-3-yn-2-ol
c) 6-chloromethyl-2-methyl-1,6-heptadien-3-yne
d) 7-chloro-2,6-dimethyl-1,5-heptadien-3-yne
e) 2-chloromethyl-6-methyl-1-heptene
f) 1-chloro-2,6-dimethyl-2-heptene
g) 2-chloromethyl-6-methyl-1,5-heptadiene
h) 1-chloro-2,6-dimethyl-2,5-heptadiene
i) 2-chloromethyl-6-methyl-1,6-heptadiene
j) 6-chloromethyl-2-methyl-1,5-heptadiene (7-chloro-2,6-dimethyl-1,5-heptadiene).

D. Preferred Route to the C-18 Ketone Precursor of Phytol.

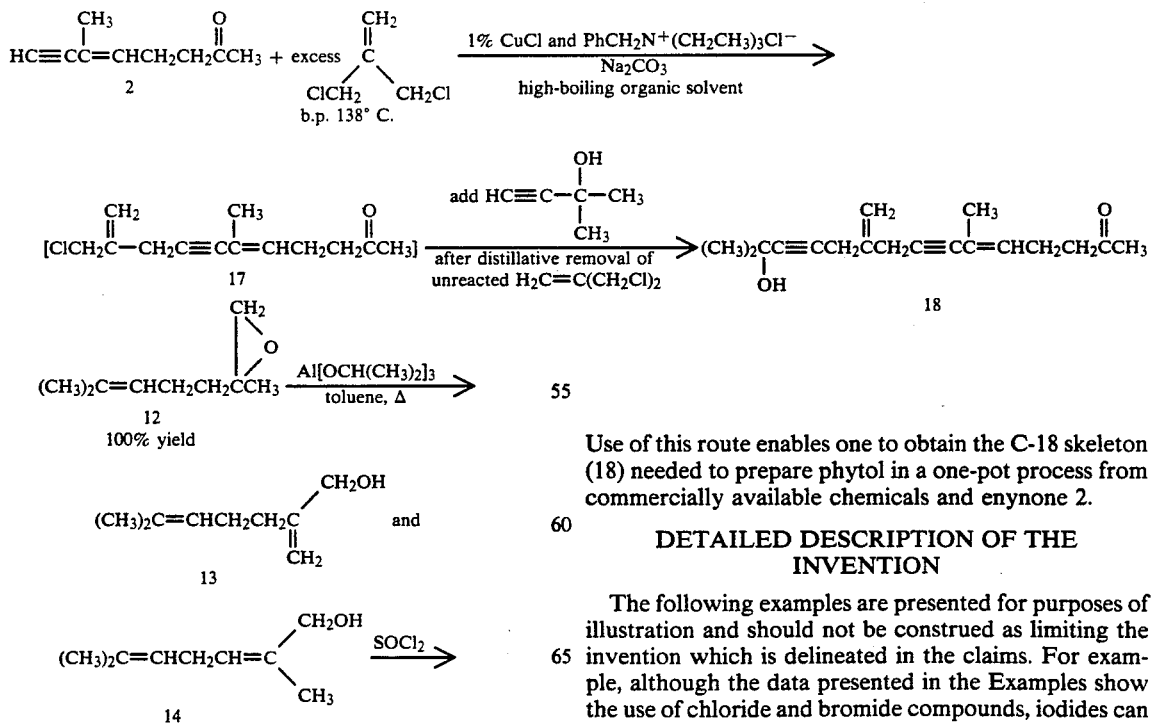

Use of this route enables one to obtain the C-18 skeleton (18) needed to prepare phytol in a one-pot process from commercially available chemicals and enynone 2.

DETAILED DESCRIPTION OF THE INVENTION

The following examples are presented for purposes of illustration and should not be construed as limiting the invention which is delineated in the claims. For example, although the data presented in the Examples show the use of chloride and bromide compounds, iodides can also be employed in this process.

EXAMPLE I

Preparation of 5-Bromo-3-methyl-3-penten-1-yne

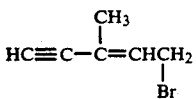

To a solution of 2.00 g (20.8 mmoles) of trans-3-methyl-2-penten-4-yn-1-ol (commercially available from Aldrich Chemical Co., Milwaukee, Wis.) in 5.00 mL of anhydrous ether, protected from atmospheric moisture and maintained at a temperature of approximately 5° C. by use of an external ice water bath, was added dropwise over a period of 15 minutes a solution of 2.00 mL (21 mmoles) of phosphorus tribromide in 10.00 mL of anhydrous ether. This mixture was subsequently stirred in the cold for 90 minutes, after which it was transferred using a small amount of hexane to a flask containing 25 mL of ice water in order to destroy excess $PBr_3$. [NOTE: On a larger scale, this step would not be necessary since one mole of phosphorus tribromide is known to be consumed by reaction with three moles of a primary alcohol.] After the addition of 25 mL of saturated brine, the layers were separated and the organic layer was washed in successive order with saturated aqueous sodium bicarbonate (25 mL) and saturated brine (25 mL). The washed organic layer was then dried over anhydrous magnesium sulfate and filtered. Removal of the ether and hexane under reduced pressure afforded 2.99 g (90% yield) of the named allylic bromide. Due to its anticipated reactivity and known lachrymatory properties, it was treated immediately with 2,4-pentanedione as described in Example II. On a larger scale, it may be desirable to combine the transformations outlined in Examples I and II in a "one-pot" process, thereby avoiding the isolation of this allylic bromide.

EXAMPLE II

Preparation of 5-octen-7-yn-2-one

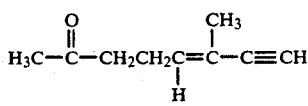

In accordance with a procedure suggested by L. Miginiac, et al., Org. Prep. Proced. Int., 10, 261 (1978), a mixture containing 2.81 g (17.7 mmoles) of 5-bromo-3-methyl-3-penten-1-yne (produced in accordance with Example I), 3.27 g (23.6 mmoles) of anhydrous potassium carbonate, and 2.00 mL (19.5 mmoles) of 2,4-pentanedione (purchased from Aldrich Chemical Co., Milwaukee, Wis.) in 12.0 mL of absolute ethanol was heated, protected from atmospheric moisture, at reflux for 19 hours. The cooled mixture was diluted with 60 mL of water to dissolve the inorganic solids and the product was isolated by extraction (3×60 mL) with 1:1 (v/v) ether:hexane. After subsequent washing of the combined organic extracts with 10% aqueous sodium chloride (3×80 mL), the organic layer was dried over anhydrous magnesium sulfate and filtered. Removal of the volatile organic solvents by evaporation at reduced pressure, followed by evaporative distillation, afforded 1.67 g (69% yield) of the named ketone: boiling point 82°–91° C. (bath temperature, 2.5 mm). The identity and purity of this known ketone were ascertained by IR and proton NMR analysis. An alternate synthesis of this ketone has been described by P. I. Zakharova, et al., Chem. Abstracts. 75, 109784h (1971).

EXAMPLE III

Preparation of 10-Chloromethyl-6-methyl-5,10-undecadien-7-yn-2-one

A mixture of 120 mg (0.88 mmole) of 6-methyl-5-octen-7-yn-2-one (produced in accordance with Example II), 2.00 mL (19 mmoles, the excess of which can be quantitatively recovered by distillation at reduced pressure after the reaction is complete) of 3-chloro-2-chloromethyl-1-propene (purchased from Aldrich Chemical Co., Milwaukee, Wis.), 193 mg (1.4 mmoles) of anhydrous potassium carbonate, 20 mg (0.20 mmole) of cuprous chloride, and 20 mg (0.087 mmole) of benzyltriethylammonium chloride in 2.00 mL of acetonitrile (HPLC-grade, purchased from Aldrich Chemical Co., Milwaukee, Wis.) was stirred vigorously at room temperature for 22 hours, during which time the mixture was maintained under an atmosphere of nitrogen. The mixture was then diluted with 40 mL of 1:1 (v/v) ether:hexane and filtered through a small pad of Hyflo Super-Cel ® filtering aid. The filtrate was washed with 20 mL of 5% aqueous sodium chloride, then dried over anhydrous magnesium sulfate, and re-filtered. Removal of the volatile organic material by evaporation at reduced pressure (50 mm) and recovery of unreacted 3-chloro-2-chloromethyl-1-propene by evaporative fractional distillation at reduced pressure (2.5 mm) afforded 146 mg (74% yield) of the named ketone after distillation in the presence of a small amount of calcium carbonate: boiling point 122°–130° C. (bath temperature, 0.20 mm). Proton NMR analysis indicated the presence of a minor impurity, subsequently found to have been present as a contaminant in 3-chloro-2-chloromethyl-1-propene. The named ketone was characterized by a singlet at δ1.78 ($CH_3$ bonded to C-6), a singlet at δ2.12 ($CH_3C=O$), a singlet at δ3.15 (2 hydrogens bonded to C-9), and a singlet at δ4.05 ($CH_2Cl$).

EXAMPLE IV

Preparation of 14-Hydroxy-6,14-dimethyl-10-methylene-5-pentadecen-7,12-diyn-2-one A mixture of 118 mg (0.52 mmole) of 10-chloromethyl-6-methyl-5,10-undecadien-7-yn-2-one (produced in accordance with Example III), 46 mg (0.55 mmole) of 2-methyl-3-butyn-2-ol (purchased from Aldrich Chemical Co., Milwaukee, Wis.), 125 mg (0.90 mmole) of anhydrous potassium carbonate, 12 mg (0.12 mmole) of cuprous chloride, and 13 mg (0.057 mmole) of benzyltriethylammonium chloride in 0.75 mL of acetonitrile (HPLC-grade, purchased from Aldrich Chemical Co., Milwaukee, Wis.) was stirred vigorously at room temperature for 25 hours, during which time the mixture was maintained under an atmosphere of nitrogen. Isolation of the product as described in the procedure of Example III afforded, after removal of the volatile organic solvents at reduced pressure, 109 mg (77% yield) of the named C-18 ketone. The proton NMR spectrum of this compound exhibited a singlet at δ1.50 [6H's, $C(CH_3)_2$], a singlet at δ1.77 ($CH_3$ bonded to C-6), a singlet at δ2.12 ($CH_3C=O$), and two singlets at δ2.97 and 3.04 (4H's, hydrogens bonded to C-11 and C-9).

Since the reaction conditions used to prepare the named ketone are virtually identical to those described in Example III, these two transformations (i.e., Examples III and IV) could probably be conducted in "one pot" without the need for isolation of 10-chloromethyl-6-methyl-5,10-undecadien-7-yn-2-one, thereby minimizing the quantities of benzyltriethylammonium chloride (or other phase-transfer catalyst) and cuprous chloride. However, to ensure removal of excess 3-chloro-2-chloromethyl-1-propene prior to the second coupling, a highboiling solvent such as 1-methyl-2-pyrrolidinone might have to be present in the reaction mixture.

EXAMPLE V

Preparation of 6-Chloromethyl-2-methyl-6-hepten-3-yn-2-ol

A mixture of 0.25 mL (2.58 mmoles) of 2-methyl-3-butyn-2-ol, 1.00 mL (9.5 mmoles) of 3-chloro-2-chloromethyl-1-propene (purchased from Aldrich Chemical Co., Milwaukee, Wis.), 632 mg (4.57 mmoles) of anhydrous potassium carbonate, 22 mg (0.22 mmole) of cuprous chloride, and 53 mg (0.23 mmole) of benzyltriethylammonium chloride in 2.00 mL of acetonitrile (HPLC-grade) was stirred vigorously at room temperature for 23 hours, during which time the mixture was maintained under an atmosphere of nitrogen. Isolation of the product as described in the procedure of Example III afforded 391 mg (88% material balance) of the named enynol, shown by proton NMR analysis to be contaminated with approximately 20-25% of the undesired bis-coupled product: 2,10-dimethyl-6-methylene-3,8-undecadiyn-2,10-diol. Formation of the latter can be minimized by use of a larger excess of 3-chloro-2-chloromethyl-1-propene, which can be recovered at the end of the reaction.

The proton NMR spectrum of the named enynol exhibited a singlet at $\delta 1.54$ [6H's, $(CH_3)_2C$], a broad singlet at $\delta 3.09$ (2 hydrogens bonded to C-5), and a singlet at $\delta 4.06$ ($CH_2Cl$).

EXAMPLE VI

Preparation of 2,6-Dimethyl-6-hepten-3-yn-2-ol Using Carbonate as the Base

Using a modification of the procedure suggested by T. Jeffery, *Tetrahedron Lett.*, 30. 2225 (1989), a mixture of 1.00 mL (10.3 mmoles) of 2-methyl-3-butyn-2-ol, 1.10 mL (11.1 mmoles) of 3-chloro-2-methylpropene (purchased from Aldrich Chemical Co., Milwaukee, Wis.), 2.46 g (17.8 mmoles) of anhydrous potassium carbonate, 86 mg (0.87 mmole) of cuprous chloride, and 204 mg (0.90 mmole) of benzyltriethylammonium chloride in 6.00 mL of acetonitrile (HPLC-grade) was stirred vigorously at room temperature for 19 hours, during which time the mixture was maintained under a nitrogen atmosphere. Isolation of the product as described in the procedure of Example III afforded, after removal of the volatile organic solvents at reduced pressure, 1.11 g (78% yield) of the named alcohol, whose proton NMR spectrum exhibited singlets at $\delta 1.51$ [6H's, $(CH_3)_2C$], $\delta 1.78$ (vinyl $CH_3$), $\delta 2.32$ (OH), $\delta 2.89$ (2 hydrogens bonded to C-5), and $\delta 4.95$ and $4.79$ (C=$CH_2$).

This coupling reaction was equally successful when tetra-n-butylammonium chloride was used as the phase-transfer catalyst in lieu of benzyltriethylammonium chloride or when cuprous iodide was used in lieu of cuprous chloride. Use of various organic solvents (e.g., N,N-dimethylformamide or ethyl acetate) in lieu of acetonitrile affected the rate of formation of the named alcohol, with solvents of moderate polarity (e.g., ethyl acetate) necessitating longer reaction times. Sodium carbonate was used as the base in lieu of potassium carbonate in one of these coupling reactions, and it proved to be equally effective.

EXAMPLE VII

Preparation of 2,6-Dimethyl-6-hepten-3-yn-2-ol In the Absence of a solvent

The coupling reaction was conducted in the manner described in the procedure of Example VI using the following reagents: 1.00 mL (10.3 mmoles) of 2-methyl-3-butyn-2-ol, 1.10 mL (11.1 mmoles) of 3-chloro-2-methylpropene, 2.34 g (16.9 mmoles) of anhydrous potassium carbonate, 89 mg (0.90 mmole) of cuprous chloride, and 165 mg (0.72 mmole) of benzyltriethylammonium chloride. Isolation of the product in the usual manner afforded 925 mg (65%) of the named alcohol, thereby demonstrating the lack of need for a solvent in this coupling reaction.

EXAMPLE VIII

Preparation of 2,6-Dimethyl-6-hepten-3-yn-2-ol In the Absence of both a Phase-Transfer Catalyst and a Solvent The coupling reaction was conducted in the manner described in the procedure of Example VI using the following reagents: 1.00 mL (10.3 mmoles) of 2-methyl-3-butyn-2-ol, 1.10 mL (11.1 mmoles) of 3-chloro-2-methylpropene, 2.40 g (17.3 mmoles) of anhydrous potassium carbonate, and 84 mg (0.85 mmoles) of cuprous chloride. Isolation of the product in the usual manner afforded 105 mg (7.4% yield) of the named alcohol. When this yield is compared with that reported in Example VII, it is evident that, in the absence of a polar solvent, the phase-transfer catalyst is desirable since it markedly accelerates the coupling. However, the presence of such a catalyst is not essential to achieve the desired transformation.

EXAMPLE IX

Preparation of 2,6-Dimethyl-6-hepten-3-yn-2-ol Using Dipotassium Hydrogen Phosphate as the Base The coupling reaction was conducted in the manner described in the procedure of Example VI using the following reagents: 1.00 mL (10.3 mmoles) of 2-methyl-3-butyn-2-ol, 1.10 mL (11.1 mmoles) of 3-chloro-2-methylpropene, 2.61 g (15.0 mmoles) of $K_2HPO_4$ (potassium phosphate, dibasic), 88 mg (0.89 mmole) of cuprous chloride, and 200 mg (0.88 mmole) of benzyltriethylammonium chloride in 3.00 mL of acetonitrile (HPLC-grade). Isolation of the product in the usual manner afforded 951 mg (67% yield) of the named alcohol.

EXAMPLE X

Preparation of a Mixture of 6-Chloromethyl-2-methyl-6-hepten-3-yn-2-ol and 7-Chloro-2,6-dimethyl-5-hepten-3-yn-2-ol In accordance With a procedure suggested by J. Gore, et al., *Tetrahedron Lett.*, 30, 5767 (1989), a solution of 0.50 mL (6.20 mmoles) of sulfuryl chloride in 15.0 mL of dichloromethane was added dropwise over a period of 25 minutes to a stirred mixture of 816 mg (5.90 mmoles) of 2,6-dimethyl-6-hepten-3-yn-2-ol (produced in accordance with Example VI) and 2.54 g (24 mmoles) of anhydrous sodium carbonate in 10.0 mL of dichloromethane at room temperature. This mixture was subsequently stirred at room temperature for an additional 75 minutes, during which time it was maintained under a nitrogen atmosphere. After the addition of 15 mL of water to dissolve the inorganic salts, the mixture was diluted with 100 mL of ether and 50 mL of 10% aqueous sodium chloride. The layers were then separated; and the organic layer was washed once with 50 mL of saturated brine, then dried over anhydrous sodium sulfate, and filtered. Removal of the volatile organic solvents by evaporation at reduced pressure afforded 955 mg (94% yield) of a 1:1 mixture of the two named allylic chlorides, both of which can be used in a synthesis of phytol. The proton NMR spectrum of this mixture exhibited two singlets of equal intensity at $\delta 4.22$ (CH$_2$Cl of 7-chloro-2,6-dimethyl-5-hepten-3-yn-2-ol) and $\delta 4.06$ (CH$_2$Cl for 6-chloromethyl-2-methyl-6-hepten-3-yn-2-ol). Also present in this crude product mixture was a minor amount (approximately 15%) of what appeared to be 6,7-dichloro-2,6-dimethyl-3-heptyn-2-ol, derived from addition of chlorine to the double bond in the starting enynol.

EXAMPLE XI

Preparation of
14-Hydroxy-6,14-dimethyl-10-methylene-5-pentadecen-7,12-diyn-2-one and 14-Hydroxy-6,10,14-trimethyl-5,10-pentadecadien-7,12-diyn-2-one A mixture of 446 mg (2.58 mmoles) of 6-chloromethyl-2-methyl-6-hepten-3-yn-2-ol and 7-chloro-2,6-dimethyl-5-hepten-3-yn-2-ol (produced in accordance with Example X), 264 mg (1.94 mmoles) of 6-methyl-5-octen-7-yn-2-one (produced in accordance with Example II), 539 mg (3.90 mmoles) of anhydrous potassium carbonate, 20 mg (0.20 mmoles) of cuprous chloride, and 46 mg (0.20 mmoles) of benzyltriethylammonium chloride in 2.00 mL of acetonitrile (HPLC-grade) was stirred vigorously at room temperature for 18 hours, during which time the mixture was maintained under a nitrogen atmosphere. Isolation of the product in the manner described in the procedure of Example III afforded 556 mg of material, proton NMR analysis of which indicated the presence of minor amounts of unreacted 7-chloro-2,6-dimethyl-5-hepten-3-yn-2-ol and 6-methyl-5-octen-7-yn-2-one, but not any of the nonconjugated allylic chloride (6-chloromethyl-2-methyl-6-hepten-3-yn-2-ol) which presumably underwent the coupling reaction more readily. Removal of the C-9 components by evaporative fractional distillation in the presence of a small amount of powdered calcium carbonate, followed by distillation, afforded 211 mg (40% yield, not corrected for recovery of unreacted starting materials) of the two named C-18 ketones: boiling point 130°–145° C. (bath temperature, 0.25 mm).

EXAMPLE XII

Preparation of
6-Chloromethyl-2-methyl-1,6-heptadien-3-yne and

7-Chloro-2,6-dimethyl-1,5-heptadien-3-yne

To a solution of 2.25 mL (16.1 mmoles) of triethylamine in 5.00 mL of dichloromethane containing 975 mg (5.65 mmoles) of a 1:1 mixture of 6-chloromethyl-2-methyl-6-hepten-3-yn-2-ol and 7-chloro-2,6-dimethyl-5-hepten-3-yn-2-ol (produced in accordance with Example X), protected from atmospheric moisture and maintained at a temperature of approximately 5° C. by use of an external ice water bath, was added 0.75 mL (9.7 mmoles) of methanesulfonyl chloride. This mixture was subsequently stirred in the cold for 3.5 hours, after which several ice chips were added to quench the reaction. After dilution with 25 mL of ether, the organic layer was washed in successive order with 1:1 (volume/volume) 2M aqueous hydrochloric acid: saturated brine (2×40 mL), saturated aqueous sodium bicarbonate (1×25 mL), and saturated brine (1×25 mL). The washed organic layer was subsequently dried over anhydrous magnesium sulfate and filtered. Removal of the volatile organic material by evaporation at reduced pressure, followed by evaporative distillation, afforded 554 mg (63% yield) of the two named allylic chlorides: boiling point 68°–77° C. (bath temperature, 0.70 mm). The proton NMR spectrum of this mixture exhibited two singlets of equal intensity at $\delta 4.26$ (CH$_2$Cl of 7-chloro-2,6-dimethyl-1,5-heptadien-3-yne) and $\delta 4.10$ (CH$_2$Cl of 6-chloromethyl-2-methyl-1,6-heptadien-3-yne). The latter allylic chloride can also be obtained by dehydration of 6-chloromethyl-2-methyl-6-hepten-3-yn-2-ol (produced in accordance with Example V) in a similar manner.

EXAMPLE XIII

Preparation of
6,14-Dimethyl-10-methylene-5,14-pentadecadien-7,12-diyn-2-one

Using a modification of the procedure suggested by T. Jeffery, *Tetrahedron Lett.*, 30, 2225 (1989), a mixture of 175 mg (1.13 mmoles) of 6-chloromethyl-2-methyl-1,6-heptadien-3-yne (produced in accordance with Example XII), 139 mg (1.02 mmoles) of 6-methyl-5-octen-7-yn-2-one (produced in accordance with Example II), 220 mg (1.6 mmoles) of anhydrous potassium carbonate, 50 mg (0.50 mmole) of cuprous chloride, and 30 mg (0.13 mmole) of benzyltriethylammonium chloride in 1.00 mL of acetonitrile (HPLC-grade) was stirred vigorously at room temperature for 21 hours, during which time the mixture was maintained under a nitrogen atmosphere. Isolation of the product as described in the procedure of Example III afforded, after fractional evaporative distillation, 207 mg (80% yield) of the named unsaturated ketone: boiling point 122°–135° C. (bath temperature, 0.25 mm). The identity and purity of this compound were ascertained by highfield (300 MHz) proton NMR analysis. The proton NMR spectrum of the named ketone exhibited singlets at $\delta 1.77$ and 1.86 (two vinyl CH$_3$'s), a singlet at $\delta 2.12$ (CH$_3$C=O), a triplet (J=7.3Hz) at $\delta 2.47$ (CH$_2$C=O), two singlets at $\delta 3.08$ and 3.09 (4H's, hydrogens bonded to C-9 and C-11), a singlet at $\delta 5.15$ (3 vinyl H's), a singlet at $\delta 5.21$ (one vinyl H), and a triplet at $\delta 5.70$ (vinyl hydrogen bonded to C-5).

EXAMPLE XIV

Preparation of 6-Methyl-2-heptanone

A mixture of 1.27 g (9.76 mmoles) of 6-methyl-2-heptanol (purchased from Aldrich Chemical Co., Milwaukee, Wis.) and 9.26 g (42.9 mmoles) of pyridinium chlorochromate (purchased from Aldrich Chemical Co., Milwaukee, Wis.) in 35 mL of dichloromethane was stirred at room temperature for 3.5 hours. At that point, the mixture was diluted with 150 mL of ether and 200 mL of 1M aqueous sodium hydroxide. After separating the layers, the organic layer was washed in successive order with 9:1 (volume/volume) 1M aqueous sodium hydroxide: saturated brine (2×100 mL), 10% aqueous sodium chloride (1×100 mL), 3:1 (volume/volume) 2M aqueous hydrochloric acid: saturated brine (3×100 mL), saturated aqueous sodium bicarbonate (1×100 mL), and saturated brine (1×100 mL). The organic layer was then dried over anhydrous magnesium sulfate and filtered. Removal of the volatile organic solvents by evaporation at reduced pressure afforded 1.214 g (97% yield) of the named ketone. The identity and purity of this known compound were ascertained by IR and proton NMR analysis.

On a larger scale, the named ketone can be readily obtained by catalytic hydrogenation ($H_2$/Pd-C) of the commercially available 6-methyl-5-hepten-2-one.

EXAMPLE XV

Preparation of 2-Methyl-2-[4-methylpentyl]oxirane

Using a modification of the procedure suggested by R. Gree, et al., *Synth. Commun.*, 15, 749 (1985), a mixture of 1.03 g (8.03 mmoles) of 6-methyl-2-heptanone (produced in accordance with Example XIV), 246 mg (1.08 mmoles) of benzyltriethylammonium chloride, and 5.86 g (31.1 mmoles) of trimethylsulfonium methylsulfate (purchased from Aldrich Chemical Co., Milwaukee, Wis.) in 14 mL of dichloromethane and 14 mL of 72% (weight/volume) aqueous sodium hydroxide was stirred vigorously at room temperature for 22 hours, during which time the mixture was maintained under a nitrogen atmosphere. In order to isolate the product, the mixture was cooled to a temperature of approximately 15° C. by use of an external cold water bath, and diluted with 35 mL of water and 60 mL of hexane. After separating the layers, the organic layer was washed with 25 mL of saturated brine, dried over anhydrous sodium sulfate, and then filtered. Removal of the volatile organic solvents by evaporation at reduced pressure afforded 1.10 g (96.5% yield) of the named epoxide, the identity and purity of which were ascertained by IR and proton NMR analysis.

EXAMPLE XVI

Preparation of 6-Methyl-2-methylene-1-heptanol and 2,6-Dimethyl-2-hepten-1-ol

Using a procedure suggested by S. Terao, et al., *Synthesis*, 467 (1979), a mixture of 521 mg (3.66 mmoles) of 2-methyl-2-[4-methylpentyl]oxirane (produced in accordance with Example XV) and 1.73 g (8.47 mmoles of aluminum isopropoxide in 10 mL of toluene was heated at reflux for 3.75 hours. [Note: On a larger scale, the isopropyl alcohol formed during the reaction can be continuously removed by fractional distillation, thereby enabling one to use considerably less aluminum isopropoxide to effect this isomerization.] After cooling to room temperature, the reaction mixture was treated with 15 mL of 2M aqueous hydrochloric acid to decompose the aluminum complex. The mixture was subsequently diluted with 25 mL of ether and 30 mL of 10% aqueous sodium chloride. After separating the layers, the organic layer was washed in successive order with 10% aqueous sodium chloride (1×25 mL) and saturated brine (1×25 mL), and then was dried over anhydrous sodium sulfate and filtered. Removal of the volatile organic solvents by evaporation at reduced pressure afforded, after evaporative distillation, 482 mg (93% yield) of the named allylic alcohols: boiling point 58°-71° C. (bath temperature, 0.20 mm). Proton NMR analysis indicated that the product was a 2:1 mixture of 6-methyl-2-methylene-1-heptanol and 2,6-dimethyl-2-hepten-1-ol respectively, accompanied by approximately 10% of what appeared to be a saturated C-9 alcohol (2,6-dimethyl-1-heptanol). 2,6-Dimethyl-2-hepten-1-ol was characterized by two singlets at δ4.09 ($CH_2OH$, E stereoisomer), and 3.94 ($CH_2OH$, Z stereoisomer), and two triplets at δ5.37 and 5.24 (vinyl H, Z and E stereoisomers). The corresponding signals for 6-methyl-2-methylene-1-heptanol appeared as singlets at δ4.02 ($CH_2OH$), 4.97 (one vinyl H), and 4.81 (the second vinyl H).

EXAMPLE XVII

Preparation of 2-Chloromethyl-6-methyl-1-heptene and

1-Chloro-2,6-dimethyl-2-heptene

Using a procedure suggested by A. I. Meyers, et al., *J. Org. Chem.*, 36, 3044 (1971), to a mixture of 1.00 mL (7.17 mmoles) of triethylamine, 157 mg (3.70 mmoles) of lithium chloride and 457 mg (3.21 mmoles) of a mixture of 6-methyl-2-methylene-1-heptanol and 2,6-dimethyl-2-hepten-1-ol (produced in accordance with Example XVI) in 6.0 mL of N,N-dimethylformamide (spectrophotometricgrade, purchased from Aldrich Chemical Co., Milwaukee, Wis.), protected from atmospheric moisture and maintained at a temperature of approximately 5° C. by use of an external ice water bath, was added 0.50 mL (6.46 mmoles) of methanesulfonyl chloride. This mixture was subsequently stirred in the cold for 5 hours, after which several ice chips were added to quench the reaction. After dilution with 40 mL of 1:1 (v/v) hexane:ether, the organic layer was washed in successive order with 10% aqueous sodium chloride (1×50 mL), 1:1 (volume/volume) 2M aqueous hydrochloric acid: saturated brine (2×50 mL), 10% aqueous sodium chloride (1×50 mL), saturated aqueous sodium bicarbonate (1×50 mL), and saturated brine (1×50 mL). The washed organic layer was subsequently dried over anhydrous magnesium sulfate and filtered. Removal of the volatile organic material by evaporation at reduced pressure, followed by evaporative distillation, afforded 407 mg (79% yield) of the two named allylic chlorides: boiling point 57°-64° C. (bath temperature, 0.40 mm). The identity and purity of this product mixture were ascertained by high-field (300 MHz) proton NMR analysis. 2-Chloromethyl-6-methyl-1-heptene was characterized by singlets at δ5.09 (one vinyl H), 4.93 (the second vinyl H), and 4.02 ($CH_2Cl$). The corresponding signals for 1-chloro-2,6-dimethyl-2-heptene appeared as two triplets at δ5.50 and 5.35 (one vinyl H, Z and E stereoisomers) and two singlets at δ4.05 ($CH_2Cl$, E stereoisomer) and 4.00 ($CH_2Cl$, Z stereoisomer).

Although this methodology was quite successful in converting the starting primary allylic alcohols to the corresponding allylic chlorides, on a larger scale it would be preferred to use a less costly reagent such as thionyl chloride to effect the same transformation.

EXAMPLE XVIII

Preparation of
6-Methyl-10-[4-methylpentyl]-5,10-undecadien-7-yn-2-one and 6,10,14-Trimethyl-5,10-pentadecadien-7-yn-2-one A mixture of 155 mg (0.965 mmole) of 2-chloromethyl-6-methyl-1-heptene and 1-chloro-2,6-dimethyl-2-heptene (produced in accordance with Example XVII), 137 mg (1.01 mmoles) of 6-methyl-5-octen-7-yn-2-one (produced in accordance with Example II), 223 mg (1.61 mmoles) of anhydrous potassium carbonate, 20 mg (0.20 mmole) of cuprous chloride, and 23 mg (0.10 mmole) of benzyltriethylammonium chloride in 1.00 mL of acetonitrile (HPLC-grade) was stirred vigorously at room temperature for 20 hours, during which time the mixture was maintained under a nitrogen atmosphere. Isolation of the product in the manner described in the procedure of Example III afforded, after fractional evaporative distillation, 184 mg (73% yield) of the two named unsaturated ketones: boiling point 122°-138° C. (bath temperature, 0.25 mm). The proton NMR spectrum of 6-methyl-10-[4-methylpentyl]-5,10-undecadien-7-yn-2-one exhibited a doublet (J=6.6Hz) at $\delta 0.88$ [6H's, $(CH_3)_2C$], a singlet at $\delta 1.79$ (vinyl $CH_3$ bonded to C-6), a singlet at $\delta 2.13$ ($CH_3C=O$), a singlet at $\delta 2.97$ (two hydrogens bonded to C-9), two singlets at $\delta 4.78$ and 5.00 (two vinyl H's, $C=CH_2$), and a triplet at $\delta 5.65$ (vinyl H bonded to C-5). The presence of 6,10,14-trimethyl-5,10-pentadecadien-7-yn-2-one as the other compound in the product mixture was indicated by two triplets at $\delta 5.35$ and 5.15 (vinyl H bonded to C-11, Z and E stereoisomers) on the proton NMR spectrum. There is no need to separate these two C-18 unsaturated ketones, since catalytic hydrogenation ($H_2$/Pd-C in ethanol) will yield the same product in both cases: 6,10,14-trimethyl-2-pentadecanone. The latter ketone has previously been converted to phytol by F. G. Fischer and K. Lowenberg [*Ann.*, 475, 183 (1929)].

EXAMPLE XIX

Preparation of
2-Methyl-2-[4-methyl-3-pentenyl]oxirane

The reaction was conducted in the manner described in the procedure of Example XV using the following reagents: 1.00 mL (6.78 mmoles) of 6-methyl-5-hepten-2-one (purchased from Aldrich Chemical Co., Milwaukee, Wis.), 2.58 g (13.7 mmoles) of trimethylsulfonium methylsulfate, 170 mg (0.75 mmole) of benzyltriethylammonium chloride, 10 mL of dichloromethane, and 10 mL of 72% (weight/volume) aqueous sodium hydroxide. Isolation of the product as described in the procedure of Example XV afforded 930 mg (98% yield) of the named epoxide, the identity and purity of which were ascertained by IR and proton NMR analysis.

EXAMPLE XX

Preparation of 6-Methyl-2-methylene-5-hepten-1-ol and 2,6-Dimethyl-2,5-heptadien-1-ol The isomerization reaction was conducted in the manner described in the procedure of Example XVI using the following reagents: 401 mg (2.86 mmoles) of 2-methyl-2-[4-methyl-3-pentenyl]oxirane (produced in accordance with Example XIX), 1.36 g (6.66 mmoles) of aluminum isopropoxide, and 8.00 mL of toluene. Isolation of the product as described in the procedure of Example XVI afforded, after evaporative distillation, 380 mg (95% yield) of the two named allylic alcohols, both of which can be used to synthesize phytol: boiling point 78°-83° C. (bath temperature, 0.25 mm). Proton NMR analysis indicated that the product was a 2:1 mixture of 6-methyl-2-methylene-5-hepten-1-ol and 2,6-dimethyl-2,5-heptadien-1-ol respectively, accompanied by approximately 10% of what appeared to be 2,6-dimethyl-5-hepten-1-ol. 2,6-Dimethyl-2,5-heptadien-1-ol was characterized by two singlets at $\delta 4.11$ ($CH_2OH$, E stereoisomer) and 3.95 ($CH_2OH$, Z stereoisomer). The corresponding signal for 6-methyl-2-methylene-5-hepten-1-ol appeared as a singlet at $\delta 4.01$ ($CH_2OH$).

6-Methyl-2-methylene-5-hepten-1-ol was previously synthesized in one step using 1-chloro-3-methyl-2-butene and 2-methyl-2-propen-1-ol. See: S. Takano, et al., *Chem. Lett.*, 1261 (1984). 2,6-Dimethyl-2,5-heptadien-1-ol has been prepared by J. F. Normant, et al., *Synthesis*, 528 (1978).

EXAMPLE XXI

Preparation of
2-Chloromethyl-6-methyl-1,5-heptadiene and

1-Chloro-2,6-dimethyl-2,5-heptadiene

The reaction was conducted in the manner described in the procedure of Example XVII using the following reagents: 360 mg (2.57 mmoles) of a mixture of 6-methyl-2-methylene-5-hepten-1-ol and 2,6-dimethyl-2,5-heptadien-1-ol (produced in accordance with Example XX), 124 mg (2.92 mmoles) of lithium chloride, 0.60 mL (4.3 mmoles) of triethylamine, 4.0 mL of N,N-dimethylformamide (spectrophotometric-grade) and 443 mg (3.87 mmoles) of methanesulfonyl chloride. Isolation of the product as described in the procedure of Example XVII afforded, after evaporative distillation, 271 mg (66% yield) of the two named allylic chlorides: boiling point 58°-65° C. (bath temperature, 0.50 mm). The proton NMR spectrum of the product exhibited singlets at $\delta 4.02$ ($CH_2Cl$, 2-chloromethyl-6-methyl-1,5-heptadiene) and $\delta 4.06$ and 3.98 ($CH_2Cl$, E and Z stereoisomers of 1-chloro-2,6-dimethyl-2,5heptadiene).

The novel C-9 compounds 2-chloromethyl-6-methyl-1,6-heptadiene and 6-chloromethyl-2-methyl-1,5-heptadiene can be obtained in three steps from 6-methyl-6-hepten-2-one in the same manner that 2-chloromethyl-6-methyl-1,5-heptadiene and 1-chloro-2,6-dimethyl-2,5heptadiene were prepared, starting with the commercially available 6-methyl-5-hepten-2-one. The location of the isolated double bond (which is remote from the allylic chloride functionality) should have no effect on the coupling reaction (to yield the desired C-18 unsaturated ketones) and indeed that carbon-carbon double bond is ultimately hydrogenated.

EXAMPLE XXII

Preparation of
6,14-Dimethyl-10-methylene-5,13-pentadecadien-7-yn-2-one and 6,10,14-trimethyl-5,10,13-pentadecatrien-7-yn-2-one The coupling reaction was conducted in the manner described in the procedure of Example XVIII using the following reagents: 162 mg (1.02 mmoles) of a mixture of 2-chloromethyl-6-methyl-1,5-heptadiene and 1-chloro-2,6-dimethyl-2,5-heptadiene (produced in accordance with Example XXI), 138 mg (1.01 mmoles) of 6-methyl-5-octen-7-yn-2-one (produced in accordance with Example II), 232 mg (1.68 mmoles) of anhydrous potassium carbonate, 9 mg (0.09 mmole) of cuprous chloride, and 20 mg (0.088 mmole) of benzyltriethylammonium chloride in 1.00 mL of acetonitrile (HPLC-grade). Isolation of the product in the manner described in the procedure of Example III afforded 242 mg (93% yield) of material, shown by proton NMR analysis to contain a minor amount (approximately 25%) of unreacted starting ketone and allylic chlorides. Fractional evaporative distillation afforded 136 mg (52% yield, not corrected for recovery of starting materials) of the named unsaturated C-18 ketones: boiling point 115°–128° C. (bath temperature, 0.20 mm). The identity of this product mixture was confirmed by high-field (300 MHz) proton NMR analysis.

EXAMPLE XXIII

Preparation of 2-Methyl-6-hepten-3-yn-2-ol

The coupling reaction was conducted in the manner described in the procedure of Example VI using the following reagents: 1.00 mL (10.3 mmoles) of 2-methyl-3-butyn-2-ol, 1.00 mL (11.6 mmoles) of allyl bromide (3-bromopropene), 2.21 g (16.0 mmoles) of anhydrous potassium carbonate, 93 mg (0.94 mmoles) of cuprous chloride, and 207 mg (0.91 mmole) of benzyltriethylammonium chloride in 3.00 mL of acetonitrile (HPLC-grade). Isolation of the product in the manner described in the procedure of Example III afforded, after removal of the volatile organic solvents at reduced pressure, 765 mg (60% yield) of the named alcohol, the identity and purity of which were ascertained by IR and proton NMR analysis.

EXAMPLE XXIV

Preparation of 6,10-Dimethyl-2-undecanone: Hydrogenation of Carbon-Carbon Double Bonds in the Presence of a Ketone Catalytic hydrogenation of 6,10-dimethyl-3,5,9-undecatrien-2-one, also known as pseudoionone (17.8 g, 92.6 mmoles, purchased from Pfaltz & Bauer, Waterbury, Conn.) was effected over 5% palladium on activated carbon (1.01 g) at room temperature and 2-3 atmospheres ($H_2$ pressure) using ethyl alcohol (50 mL) as a solvent. After 30 minutes, the catalyst was removed by filtration through a small pad of Hyflo Super-Cel ® filtering aid. After dilution of the filtrate with 500 mL of water, the product was isolated by extraction (3×75 mL) with hexane. The combined extracts were dried over anhydrous magnesium sulfate and filtered. Removal of the volatile organic solvents by evaporation at reduced pressure, followed by distillation, afforded 15.95 g (87% yield) of the named ketone: boiling point 68°–72° C. at 0.15 mm. The identity of this known ketone was ascertained by proton NMR analysis. For use of this ketone to prepare phytol see: F. G. Fischer and K. Lowenberg, *Ann.*, 475, 183 (1929).

What is claimed is:

1. A method of synthesizing unsaturated C-18 ketones which comprises forming a reaction mixture of the following:

a) one equivalent of a C-9 primary allylic halide having the formula:

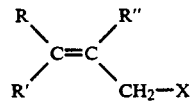

wherein X is a halide group; the R and R' substituents are either both H, or one such substituent is H and the other is a C-5 group selected from: $(CH_3)_2C(OH)C\equiv C-$, $CH_2=C(CH_3)C\equiv C-$, $(CH_3)_2CHCH_2CH_2-$, $CH_2=C(CH_3)CH_2CH_2-$, and $(CH_3)_2C=CHCH_2-$; R" is a C-6 group selected from: $(CH_3)_2C(OH)C\equiv CCH_2-$, $CH_2=C(CH_3)C\equiv CCH_2-$, $(CH_3)_2CHCH_2CH_2CH_2-$, $(CH_3)_2C=CHCH_2CH_2-$ and $CH_2=C(CH_3)CH_2CH_2CH_2-$, or R" is $CH_3-$;

(b) one equivalent of a C-9 terminal alkyne selected from the group consisting of:

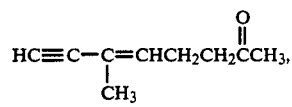

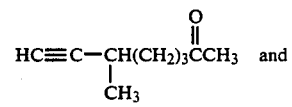

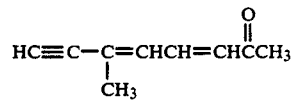

(c) a catalyst comprising a copper (I) salt; and
   (d) a base.

2. The method of claim 1 wherein said reaction mixture further includes a solvent.

3. The method of claim 2 wherein said solvent is polar.

4. The method of claim 2 wherein said solvent is selected from the group consisting of: acetonitrile, 1-methyl-2-pyrrolidinone and N,N-dimethylformamide.

5. The method of claim 1 wherein said base is non-nucleophilic.

6. The method of claim 1 wherein said base is:
   a) a salt of a strong base and a weak acid; or,
   b) a tertiary amine.

7. The method of claim 1 wherein said base is selected from the group consisting of: sodium carbonate, potassium carbonate, potassium phosphate dibasic and sodium phosphate dibasic.

8. The method of claim 1 wherein said copper (I) salt comprises cuprous chloride or cuprous iodide.

9. The method of claim 1 wherein said C-9 primary allylic halide is an allylic chloride.

10. The method of claim 1 further including the step of heating said reaction mixture to greater than room temperature.

11. The method of claim 1 wherein said reaction mixture further includes a phase-transfer catalyst.

12. The method of claim 11 wherein said phase-transfer catalyst comprises a quaternary ammonium salt.

13. The method of claim 12 wherein said quaternary ammonium salt comprises benzyltriethylammonium chloride or tetrabutylammonium chloride.

14. The method of claim 1 wherein said C-9 terminal alkyne comprises an enynone.

15. The method of claim 14 wherein said enynone is 6-methyl-5-octen-7-yn-2-one.

* * * * *